United States Patent [19]

Milnes et al.

[11] 4,210,543
[45] Jul. 1, 1980

[54] USE OF HYDRAZIDOTHIOATES AS ADDITIVES FOR FUNCTIONAL FLUIDS

[75] Inventors: Frank J. Milnes, Guilford; John R. Parziale, Wallingford, both of Conn.

[73] Assignee: Olin Corporation, New Haven, Conn.

[21] Appl. No.: 956,556

[22] Filed: Nov. 1, 1978

[51] Int. Cl.² .............................................. C10M 1/48
[52] U.S. Cl. .................................. 252/46.7; 260/923; 252/78.5
[58] Field of Search ............................. 252/46.7, 78.5; 260/923

[56] References Cited
U.S. PATENT DOCUMENTS 3,574,798  4/1971  Hazy et al. ........................ 260/923

Primary Examiner—Winston A. Douglas
Assistant Examiner—Y. Harris-Smith

Attorney, Agent, or Firm—William A. Simons; Thomas P. D'Day

[57] ABSTRACT

Disclosed is the use of selected hydrazidothioates as ashless load-carrying additives for functional fluids. These hydrazidothioates have the formula:

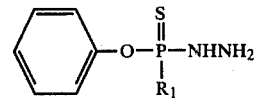

with $R_1$ being either -NHNH$_2$ or

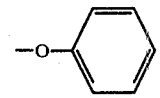

group.

5 Claims, No Drawings

USE OF HYDRAZIDOTHIOATES AS ADDITIVES FOR FUNCTIONAL FLUIDS

BACKGROUND OF THE INVENTION

1. Field of the Invention

The present invention relates to the use of selected hydrazidothioate compounds as load-carrying additives for functional fluids such as lubricants and hydraulic fluids.

2. Description of the Prior Art

The employment of chemical additives in lubricants, hydraulic oils and similar functional fluids to improve the overall load-carrying characteristics of the fluid is well known. Probably, the most commonly employed load-carrying additives are the zinc dialkyl and diaryl dithiophosphates. However, for many applications, it is necessary to employ ashless formulations (i.e. formulations that leave substantially no ash residue upon evaporation or combustion). In such instances, the above-mentioned zinc-containing compounds are not satisfactory.

Many load-carrying additives have, alternatively, been found which have this desired ashless characteristic. However, there is still a need in the art to find more suitable ashless additives. To meet this need is a primary object of the present invention.

The hydrazidothioates used in the present invention have been described in the prior art. See articles by Autenrieth and Meyer, Ber. 58, 848 (1925) and Klement and Knollmueller, Chem. Ber. 93, 1088 (1960). However, neither of these prior art references teach or suggest the present inventive use.

BRIEF SUMMARY OF THE INVENTION

The present invention, therefore, is directed to the use of selected hydrazidothioate compounds as additives for functional fluids, said hydrazide compounds having the formula:

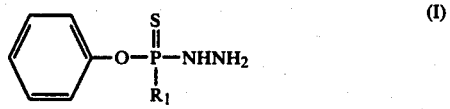

wherein $R_1$ is a $-NHNH_2$ group or a

group.

These additives improve the load-carrying characteristics of the functional fluids, while being ashless in nature.

DETAILED DESCRIPTION

The two selected hydrazidothioates of the present invention, namely O-phenyl phosphorodihydrazidothioate and O,O,diphenyl phosphorohydrazidothioate, may be made according to methods described by Klement and Knollmueller in Chem. Ber. 93, 1088 (1960). Specifically, these two additive compounds may be made the reaction of the hydrazine hydrate with either phenyl phosphorodichloridothioate or O,O-diphenyl phosphorochloridothioate. See Examples 1 and 2, below. These two particular hydrazidothioate compounds may, of course, by synthesized by other conventional methods and the present invention is not intended to be limited to any particular method of making the compound. Regardless of the method of synthesis, the desired compound may be recovered from the reaction mixture by any conventional recovery method including filtration, extraction, and recrystallization.

As previously indicated, the compounds of the present invention are substantially ashless in nature. For purposes of this invention, an ashless additive is one which shows substantially no ash when tested according to the procedure set forth in ANSI/ASTM D482-74.

It is generally considered by those skilled in this art that load-carrying additives may be divided into two classes, namely antiwear and extreme pressure additives. When two lubricated moving surfaces are lightly loaded against each other, they are separated by an elastohydrodynamic oil film; as the load increases so the oil film thickness decreases. When the oil thickness approaches the dimensions of the surface roughness, it will be penetrated by surface asperities. It is in this region that antiwear additives function by improving the oil film strength and reducing intermetallic contact.

As the load is increased further, the bulk oil film collapses and mere antiwear additives are no longer sufficient to protect the surface. In this latter region, extreme pressure (EP) additives function by reacting with the metal surface to form a compound which prevents or delays welding of the metal surfaces.

For purposes of this invention, the relative antiwear characteristics of functional fluids containing additives are determined by the test procedure set forth in ANSI/ASTM D-2276-67 (Reapproved 1977) -WEAR PREVENTIVE CHARACTERISTICS OF LUBRICATING GREASE (FOUR-BALL METHOD). Still further, for purposes of this invention, the extreme pressure properties of functional fluids containing additives are determined by the test procedure set forth in ANSI/ASTM D-2783-71 (Reapproved 1976) - MEASUREMENT OF EXTREME-PRESSURE PROPERTIES OF LUBRICATING FLUIDS (FOUR-BALL METHOD).

As functional fluid additives, the present compounds normally comprise a minor proportion by weight of the total functional fluid, with a base stock fluid normally comprising a major proportion by weight of total functional fluid. Preferably, the instant additives comprise from about 0.01% to about 10%, more preferably, from about 0.1% to about 5% by weight of the total functional fluid. These weight precents are based on the filtered functional fluid in the absence of any diluents or solvents.

Any conventional method of formulating functional fluids to employ the present additives may be used and it is not intended to limit this invention to any particular method of formulation. The additives of the present invention are particularly suitable for incorporating in functional fluids such as lubricating oil compositions and hydraulic fluid compositions.

Lubricating oil compositions include crankcase lubricating oils for spark-ignited and compression-ignited internal combustion engines, such as automobile and truck engines, marine and railroad diesel engines, and the like. Automatic transmission fluids, transaxle lubricants, gear lubricants, metal-working lubricants and other lubricating oil and grease compositions may also benefit from the incorporation therein of the additive compositions of this invention.

Hydraulic composition fluids contemplated by the present invention include hydraulic brake fluids, hydraulic steering fluids, fluids used in hydraulic lifts and jacks. Also included in the scope of this invention are hydraulic fluids used in hydraulic systems such as employed in heavy equipment and transportation vehicles including highway and construction equipment, railways, planes and aquatic vehicles.

The base fluids of such lubricating oil compositions and hydraulic fluid compositions may be composed of either natural or synthetic lubricating oils or mixtures thereof. In particular, natural lubricating oils contemplated for this invention include animal oils and vegetable oils (e.g. castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes); poly(1-hexanes), poly(1-octanes), poly(1-decene), and mixtures thereof; alkylbenzenes (e.g. dodecylbenzenes, tetradecylbenzenes, dinonylbenzenes, di-(2-ethylhexyl)-benzenes), polyphenyls (e.g. biphenyls, terphenyls, alkylated polyphenyls; alkylated diphenyl ethers and alkylated diphenyl sulfides and the derivatives, analogs and homologs thereof and the like.

Alkylene oxide homopolymers and interpolymers and derivatives thereof where some of the terminal hydroxyl groups may have been modified by esterification, etherification, constitute another class of known synthetic lubricating oils. These are exemplified by the oils prepared through polymerization of ethylene oxide or propylene oxide, the alkyl and aryl ethers of these polyoxyalkylene polymers (e.g., diphenyl ether of polyethylene glycol having a molecular weight of 500–1,000 diethyl ether of polypropylene glycol having a molecular weight of 1,000–1,500) or mono- and polycarboxylic esters of said polyethylene glycol, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids) with a variety of alcohols (e.g. butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl)sebacate, di-n-hexyl fumarate, dioctyl sebacate, diisooctyl azelate, diiodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethyl propane, pentaerythritol, dipentaerythritol, tripentaerythritol, and the like.

Silicon-based oils such as the polyalkyl-, polyaryl-, polyalkoxyl-, or polyaryloxy- siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butylphenyl)silicate, hexyl-(4-methyl-2-pentoxyl)disiloxane, poly(methyl) siloxanes, poly(methylphenyl)siloxanes). Other synthetic lubricating oils include liquid esters of phosphorus-containing acids (e.g., tricresyl phosphate, trioctyl phosphate, diethyl ester of decane phosphonic acid), polymeric tetrahydrofurans and the like.

Unrefined, refined and rerefined oils, either natural or synthetic (as well as mixtures of two or more of any of these) of the type disclosed hereinabove may be used as the base stock of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, secondary distillation, acid or base extraction, filtration, percolation. Rerefined oils are obtained by processes, similar to those used to obtain refined oils, applied to refined oils which have been already used in service. Such rerefined oils are also known as reclaimed or reprocessed oils and often are additionally processed by techniques directed to removal of spent additives and oil breakdown products.

The compounds of Formula I of this invention may be used alone or in combination with other lubricant additives such as detergents, dispersants, pour-point depressing agents, antifoam agents, viscosity modifiers, other extreme pressure load-bearing agents, corrosion inhibitors, antiwear agents, antioxidants and the like.

These additional additives are well known in the art and a brief survey of conventional additives for lubricating compositions is contained in the publications LUBRICANT ADDITIVES, C. V., Smalheer and R. Kennedy Smith, published by Lezius-Hiles Co., Cleveland Ohio, 1967, and LUBRICANT ADDITIVES, M. W. Ranney, published by Noyes Data Corp., Park Ridge, N.J., 1973, which are herein incorporated by reference in their entirety.

The ash-containing detergents are well known neutral and basic alkali or alkaline earth metal salts of sulfonic acids, carboxylic acids or organophosphorus-containing acids. These phosphorus-containing acids are characterized by at least one direct carbon-to-phosphorus linkage, and can be prepared by treating an olefin polymer, i.e., polyisobutylene, with a phosphorizing agent such as phosphorus trichloride, phosphorus heptasulfide, phosphorus pentasulfide, phosphorous trichloride and sulfur, white phosphorus and a sulfur halide, or phosphorothioic chloride, When used as an ash-containing detergent, the most commonly used salts of these acids are the sodium, potassium, lithium, calcium, magnesium, strontium, and barium salts. The calcium and barium salts are used more extensively than the others. The "basic salts" are those metal salts known in the art wherein the metal is present in a stoichiometrically larger amount than that necessary to neutralize the acid. The calcium and the barium overbased petrosulfonic acids are typical examples of such basic salts. The ashless dispersants are also a well known class of materials used as additives for lubricating oils and fuels. They are particularly effective as dispersants at lower temperatures. The hydrocarbon-substituted succinic acids and their derivatives can be used as stabilizing agents in the preparation of the lubricant compositions of this invention and are representative of the dispersants. These dispersants include products obtained by the reaction of the $C_{30}$ or greater hydrocarbon-substituted succinic acid compounds and alkylene polyamines or polyhydric alcohols, which can be further post-treated with materials such as boric acids or metal compounds.

Pour-point depressing agents are illustrated by the polymers of ethylene, propylene, isobutylene, and poly-(alkylmethacrylates). Anti-foam agents include polymeric alkyl siloxanes, poly-(alkyl methacrylates), copolymers of diacetone acrylamide and alkyl acrylates or methacrylates, and the condensation products of alkyl phenol with formaldehyde and an amine. Viscosity index improvers include, polymerized and copolymerized alkyl methacrylates and polyisobutylenes.

Other extreme pressure agents, corrosion-inhibiting agents, and oxidation-inhibiting agents are exemplified by chlorinated aliphatic hydrocarbons, such as chlorinated wax; organic sulfides and polysulfides; such as benzyl disulfide, bis-(chlorobenzyl)-disulfide, dibutyl tetrasulfide, sulfurized sperm oil, sulfurized methyl ester of oleic acid, sulfurized alkyl phenol, sulfurized dipentene, sulfurized terpene, and sulfurized Diels-Alder adducts; phosphosulfurized hydrocarbons, such as the reaction product of phosphorus sulfide with terpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentyl phenyl phosphite, tridecyl phosphite, distearyl phosphite, and polypropylene substituted phenyl phosphite; metal thiocarbamates, such as zinc dioctyldithiocarbamate and barium heptylphenol dithiodicarbamate; Group II metal salts of phosphorodithioic acids, such as zinc dicyclohexyl phosphorodithioate, and the zinc salt of a phosphorodithioic acid.

The following examples are provided to further illustrate the present invention. All parts and proportions, unless otherwise explicity indicated, are by weight.

EXAMPLE I

Preparation of O-Phenyl Phosphorodihydrazidothioate

Phenyl phosphorodichloroidothioate, $C_6H_5OP(S)Cl_2$, (100 g, 0.44 mole) was added during 2.5 hours to hydrazine hydrate (225 ml of 60% solution $\simeq$141 g $N_2H_4$) stirred at 0° C. After further reaction for one hour, the mixture was filtered and the precipitate was collected, washed with 300 ml water and dried. Recrystallization from 2B ethanol (200 ml) gave 79 g of white crystals (82% yield) melting at 94°–95° C. (lit. m.p. =92°–95° C.).

EXAMPLE II

Preparation of O,O-Diphenyl Phosphorohydrazidothioate

O,O-Diphenyl phosphorochloridothioate, $(PhO)_2P(S)Cl$, (38 g, 0.13 mole) was added slowly to hydrazine hydrate, (25 g of 60% solution $\simeq$0.47 mole hydrazine) at 65°–75° C. The mixture was allowed to cool slowly and the solid product was then recovered by filtration, washed with water and dried. Recrystallization from benzene/petroleum ether (1:1) gave 30.5 g product (84% yield) melting at 59°–61° C.

EXAMPLES III–XII

The additive compounds made in Examples 1 and 2 were formulated with various commercially available base fluids, were tested in a 4-ball testers according to test procedures set forth in ANSI/ASTM D-2267-67 and ANSI/ASTM D-2783-71 to determine the antiwear and extreme pressure characteristics, respectively, of the fluids.

Two grams of each additive compound were mixed with 196 grams of a base fluid and 2 grams of an antioxidant, phenyl alpha naphthylamine, at room temperature. The mixture was then heated and stirred (e.g. at 100° F. to 250° F.) to dissolve the additive and antioxidant. The resulting solution was filtered to give a clear homogeneous fluid. After a wait of about 24 hours to ensure solubility, the solutions were tested in the 4-ball testers. The antiwear tests were conducted at 40 kg load weight, 1800 rpm, and 167° F. The results of these tests are given in Tables I and II.

TABLE I

| | FOUR-BALL ANTIWEAR TEST | | |
|---|---|---|---|
| EX. | LOAD-CARRYING ADDITIVE | BASE FLUID | AVERAGE SCAR DIAMETER |
| 3 | none | POLY-G WI-625' | 0.44 |
| 4 | O-phenyl- | POLY-G WI-625' | 0.43 |
| 5 | O,O-diphenyl- | POLY-G WI-625' | 0.34 |
| 6 | none | MONOPLEX DOS[2] | 1.81 |
| 7 | O,O-diphenyl- | MONOPLEX DOS[2] | 0.48 |

TABLE II

| | FOUR-BALL EXTREME PRESSURE TEST | | | | |
|---|---|---|---|---|---|
| EXAMPLE | LOAD-CARRYING ADDITIVE | BASE FLUID | LOAD WEAR INDEX | LAST NON-SEIZURE LOAD | WELD LOAD |
| 8 | none | POLY-G WI-625[1] | 22 | 50 | 126 |
| 9 | O-phenyl- | POLY-G WI-625[1] | 46 | 80 | 250 |
| 10 | O,O-diphenyl- | POLY-G WI-625[1] | 32 | 63 | 200 |
| 11 | none | MONOPLEX DOS[2] | 17 | 40 | 126 |
| 12 | O,O-diphenyl- | MONOPLEX DOS[2] | 40 | 100 | 160 |

[1]POLY-G WI-625 is a monobutylether of approximately 1800 molecular weight polypropylene glycol and is commercially available from the Olin Corporation.
[2]MONOPLEX DOS is a di-iso octyl sebacate and is commercially available from Rohm & Hass Company.

What is claimed is:

1. A functional fluid composition comprising a major amount of an oil of lubricating viscosity or mixtures thereof and a minor load-carrying amount of additive selected from the group of hydrazidothioates of the formula:

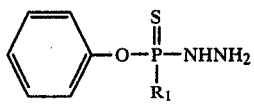

wherein $R_1$ is selected from $-NHNH_2$ and

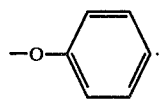

2. The functional fluid composition of claim 1 wherein said functional fluid composition is a hydraulic fluid composition.

3. The functional fluid composition of claim 1 wherein said additive is O,O-diphenyl phosphorohydrazidothioate.

4. The functional fluid composition of claim 1 wherein said additive is O-phenyl phosphorodihydrazidothioate.

5. The functional fluid composition of claim 1 wherein said additive is present in an amount from about 0.01% to about 10% by weight of said functional fluid composition.

* * * * *